US009089851B2

(12) United States Patent
Corbett et al.

(10) Patent No.: US 9,089,851 B2
(45) Date of Patent: Jul. 28, 2015

(54) DNA AMPLIFICATION APPARATUS AND METHOD

(71) Applicant: CORBETT LIFE SCIENCE PTY LTD, Hornsby (AU)

(72) Inventors: John Michael Corbett, Sanctuary Cove (AU); John Michael Corbett, Jr., Bellevue Hill (AU)

(73) Assignee: QIAGEN INSTRUMENTS AG, Hombrechtikon (CH)

( * ) Notice: Subject to any disclaimer, the term of this patent is extended or adjusted under 35 U.S.C. 154(b) by 96 days.

(21) Appl. No.: 13/677,810

(22) Filed: Nov. 15, 2012

(65) Prior Publication Data

US 2013/0071880 A1   Mar. 21, 2013

Related U.S. Application Data

(62) Division of application No. 10/516,186, filed as application No. PCT/AU03/00672 on May 30, 2003, now abandoned.

(30) Foreign Application Priority Data

May 30, 2002   (AU) ........................ PS2678

(51) Int. Cl.
 C12P 19/34      (2006.01)
 C12Q 1/68       (2006.01)
 B04B 15/02      (2006.01)
 B01L 7/00       (2006.01)

(52) U.S. Cl.
 CPC . B04B 15/02 (2013.01); B01L 7/52 (2013.01); C12Q 1/686 (2013.01); B01L 2200/147 (2013.01); B01L 2300/0803 (2013.01); B01L 2300/1844 (2013.01); B01L 2300/1872 (2013.01)

(58) Field of Classification Search
 None
 See application file for complete search history.

(56) References Cited

U.S. PATENT DOCUMENTS

| 5,656,493 | A | 8/1997 | Mullis et al. |
| 6,174,670 | B1 | 1/2001 | Wittwer et al. |
| 6,387,621 | B1 | 5/2002 | Wittwer |
| 8,226,629 | B1 * | 7/2012 | Keilman et al. ............ 604/500 |
| 2002/0058258 | A1 | 5/2002 | Wittwer et al. |
| 2003/0036054 | A1 | 2/2003 | Ladisch et al. |

FOREIGN PATENT DOCUMENTS

| WO | 9746707 A2 | 12/1997 |
| WO | 9849340 A1 | 11/1998 |

OTHER PUBLICATIONS

Chaudhari et al. (Journal of Microelectromechanical Systems, 7(4):345-355).*
Chaudhari et al. (Journal of Microelectromechanical Systems, 1998, 7(4):345-355).*
Kim et al. (J. Micromech. Microeng., 2006, 16:526-530).*
Lao et al. (Sensors and Actuators, 2000, 84:11-17).*
Beele et al., Surface Coatings Technology, 1999, vol. 120-121, p. 61-67.
Chaudhari et al., Journel of Micorelectromechanical Systems, 1998, vol. 7, No. 4, p. 345-355.
Wittwer et al., "Continuous Fluorescence Monitoring of Rapid Cycle DNA Amplification", Biotechniques, vol. 22, 1997, pp. 130-138.
Wittwer et al., "The LightCycler: A microvolume multisample fluorimeter with rapid temperature control", Biotechniques, vol. 22, 1997, pp. 176-181.
Giulietti et al., "An overview of real-time quantitative PCT: Applications to quantify cytokine gene expression." Methods: A companion to Methods in Enzymology, Academic Press Inc., NewYork, NY, vol. 25, No. 4, pp. 386-401 (Dec. 2001).
Wilhelm et al., "Influence of DNA target melting behavior on real-time PCR quantification." Clinical Chemistry, vol. 46, No. 11, pp. 1738-1743, Nov. 2000.

* cited by examiner

*Primary Examiner* — Stephanie K Mummert
(74) *Attorney, Agent, or Firm* — Miles & Stockbridge PC

(57)   ABSTRACT

The invention relates to a method for the amplification of DNA and apparatus for such amplification. The method comprises steps typically found in amplification methods but utilizes an optical procedure to detect denaturation of DNA or attain¬ment of the desired denaturation temperature. The apparatus (1) comprises a temperature controllable chamber (2) including a rotor (3) for holding a plurality of reaction vessels (see 7 for example) for reaction mixtures including DNA, a drive means for the rotor, a heater (8) within the chamber for transiently supplying infrared energy to the reaction vessels, and an optical system (12-16) for determining denaturation of at least a reference DNA or for detecting attainment of a desired denaturation temperature in at least a reference reaction vessel.

6 Claims, 4 Drawing Sheets

DNA AMPLIFICATION APPARATUS AND METHOD

CROSS REFERENCE TO RELATED APPLICATIONS

This application is a divisional application of U.S. application Ser. No. 10/516,186, filed Sep. 1, 2005, which is a §371 National Stage Application of PCT/AU2003/000672, filed May 30, 2003, which claims priority from AU PS2678 filed May 30, 2002, which are incorporated by reference in their entireties.

TECHNICAL FIELD

The invention the subject of this application relates to apparatus and methods for the amplification of DNA. In particular, the invention relates to apparatus and methods having improvements in the manner of carrying out the DNA denaturation step of the amplification process.

BACKGROUND ART

In a number of applications such as gene analysis and DNA profiling, it is desirable to multiply the amount of particular nucleic acid sequences present in a sample. For example, a duplex DNA segment of up to approximately six thousand base pairs in length may be amplified many million fold by means of the polymerase chain reaction (PCR), starting from as little as a single copy. In this technique, a denatured duplex DNA sample is incubated with a molar excess of two oligonucleotide primers, one being complementary to a first short sequence of the DNA duplex and the other being identical to a second short sequence upstream of the first short sequence (i.e., more 5' of the first short sequence).

Each primer anneals to its complementary sequence and primes the template¬dependent synthesis by DNA polymerase of a complementary strand which extends beyond the site of annealing of the other primer through the incorporation of deoxynucleotide triphosphates. Each cycle of denaturation, annealing and synthesis affords an approximate doubling of the amount of target sequence, where the target sequence is defined as the DNA sequence subtended by and including the primers. A cycle is controlled by varying the temperature to permit successive denaturation of complementary strands of duplex DNA, annealing of the primers to their complementary sequences, and primed synthesis of new complementary sequences. The use of a thermostable DNA polymerase obviates the necessity of adding new enzyme for each cycle, thus allowing automation of the DNA amplification process by thermal cycling. Twenty amplification cycles increases the amount of target sequence by approximately one million-fold.

More detailed information regarding the polymerase chain reaction can be found in standard texts such as PCR Protocols—A Guide to Methods and Application (M. A. Innis, D. H. Gelfard, J. J. Sainskey and T. J. White ed's, Academic Press, Inc., San Diego, 1990), the entire content of which is incorporated herein by cross reference.

A key step in the DNA amplification process is the denaturation step. The double stranded DNA—either as the starting material of the amplification or the product of an amplification cycle—must be denatured to allow annealing of primers for a further round of complementary strand synthesis. Without complementary stand synthesis, there is no amplification.

A number of devices have been described for carrying out DNA amplifications. For example, in U.S. Pat. No. 5,656,493 there is described a thermal cycling system in which reaction mixtures are cycled through different temperatures to effect the denaturation, annealing and polymerisation steps. The system apparatus includes a metal block having a plurality of cavities therein for holding tubes containing the reaction mixtures. The block is heated or cooled to give the temperatures required for denaturation, annealing and complementary strand synthesis.

An alternative type of device is disclosed in International Patent Application No. PCT/AU98/00277 (Publication No. WO 98/49340), in the PCT/AU98/00277 device, reaction mixture vessels are held in a rotor which rotates in a controlled temperature environment. The different temperatures required for denaturation and complementary strand synthesis are reached by heating and cooling the environment.

For efficient execution of amplification using the apparatus referred to in the previous paragraphs, operation of the apparatus is computer controlled. Other known apparatus for carrying out DNA amplifications are similarly computer controlled.

The computer control of apparatus for DNA amplification reactions includes temperature control in accordance with user defined temperatures. That is, an operator of a piece of amplification apparatus presets the temperatures at which the various steps of the amplification process will be conducted. The time at which reaction mixtures will be held at a particular temperature is also defined by the operator.

User defined times and temperatures can diminish the efficiency of an amplification process. This is particularly the case with the denaturation step where the reaction mixture may be held at the denaturation temperature far in excess of the time necessary to actually denature the DNA. The extended time taken for the denaturation step can considerably increase the overall time of an amplification. Maximising the efficiency of amplifications is of considerable importance where large numbers of amplifications need to be processed.

There is therefore a need for amplification apparatus and methods where at least the denaturation step of a DNA amplification can be carried out more efficiently.

SUMMARY OF THE INVENTION

An object of the invention is to provide a method and apparatus for DNA amplifications in which the denaturation step is executed more efficiently.

According to a first embodiment of the invention, there is provided a method for the amplification of DNA, the method comprising the steps of:

i) forming a reaction mixture comprising said DNA, an oligonucleotide primer complementary to at least one strand of said DNA, nucleotides, and a thermostable DNA polymerase;

ii) heating said mixture to denature said DNA with optical detection of denaturation or the desired denaturation temperature;

iii) on detecting denaturation of said DNA or attainment of the denaturation temperature, allowing said mixture to cool to a temperature at which primer anneals to its complementary strand;

iv) incubating said mixture at a temperature which allows synthesis of a DNA strand complementary to the strand to which said at least one primer anneals; and v) repeating steps (ii) to (iv) until the desired level of amplification is attained.

In a second embodiment, the invention provides apparatus for the amplification of DNA in a reaction mixture, the apparatus comprising:

a temperature controllable chamber including a rotor for holding a plurality of reaction vessels for reaction mixtures including DNA;

a drive means for said rotor;

a heater within said chamber for transiently supplying infrared energy to said reaction vessels; and an optical system for determining denaturation of at least a reference DNA or for detecting attainment of a desired denaturation temperature in at least a reference reaction vessel.

The principle of the method as defined above is that rather than the denaturation step being done by raising the mixture to a preset temperature and holding it at that temperature for a preset time as in known amplification protocols, the actual denaturation event is used as a control feature, or alternatively detection of the temperature at which denaturation will have occurred. This allows the denaturation step to be carried out more efficiently since depending on the DNA sample used, the denaturation temperature may vary from sample to sample. Also, the denaturation temperature may vary after repetitive denaturation cycles: when DNA has been denatured multiple times, the actual denaturation temperature will reduce.

Apparatus according to the second embodiment includes as a feature an optical system for detecting when denaturation has occurred or alternatively when the denaturation temperature has been reached. It is through this system that the denaturation event per se can control this step in an amplification rather than the step being controlled by preset temperatures and times.

With regard to the method according to the first embodiment, it will be appreciated by one of skill in the art that the mixture prepared for step (i) of the mixture is a standard amplification mixture and can include additional components such as buffers and salts normally used in amplification reactions. Commercially available reaction kits can also be used in the method. Typical reaction mixtures are described, for example in standard reference texts such as *PCR: a Practical Approach* (M J McPherson et aL, Ed's), IRL Press, Oxford, England, 1991, and numerous brochures provided by suppliers of amplification reagents and consumables.

With regard to step (ii) of the method, the optical detection of denaturation is advantageously done by measuring the fluorescence emitted by an intercalating fluorophore present in a tube containing a reference DNA or in at least one of the reaction mixtures. The reference DNA can be any convenient DNA but advantageously has a similar melting temperature to that of the DNA being amplified. It will be appreciated that with appropriate excitation of the fluorophore, emitted fluorescence will dramatically decrease at denaturation of the double stranded DNA with which the fluorophore has intercalated.

The intercalating fluorophore can be any suitable compound such as ethidium bromide or a commercially available dye such as SYBR™ Green.

The optical system can also utilise a thermochromic liquid crystal to determine when the denaturation temperature has been reached. Such crystals, which will hereafter be referred to as "TLCs", undergo a colour change at a certain temperature, the "transition temperature". The system advantageously uses a clearing point TLC in conjunction with a fluorophore. The TLC is selected to have a transition temperature that is the same or close to the denaturation temperature of the DNA to be amplified. Suitable TLCs for the foregoing purpose include high transition point custom TLCs that are designed to have a clearing point or a color transition point at approx 92-95° C.

In the TIC/fluorophore system, a vessel containing the TLC/fluorophore combination is illuminated with light that includes the excitation wavelength of the fluorophore. Below the clearing point of the TLC, there is a diminished detection of fluorescence due to blocking of emission by the TLC. At and above the transition temperature, there is as heightened detection of fluorescence due to the "clearance" of the TLC. The increase in fluorescence thus marks the temperature at which transition occurred. With appropriate selection of the TLC, attainment of the desired temperature in a reaction vessel can be detected.

TLC/fluorophore systems are described in the Australian provisional application no. PS 2677 entitled "Optical Means for Calibrating Temperature", filed 30 May 2002, the entire content of which is incorporated herein by cross reference.

In step (iii) of the method, cooling of reaction mixtures can be effected merely as a result of terminating the heating carried out in step (ii). Advantageously, however, cooling is aided by supplying a cooling agent to the environment of the reaction mixtures. This will be explained in greater detail below in connection with the apparatus of the invention. Using the apparatus of the invention, vessels containing reaction mixtures are heated by infrared energy. As a consequence of this, the chamber temperature is not raised by a significant amount and therefore cools faster than in conventional amplification procedures and apparatus.

The annealing temperature to which mixtures are cooled is selected in consideration of the primer-template combination but generally falls within the range of 50-65° C. as will be appreciated by those of skill in the art.

Step (iv) of the method is carried out in accordance with usual practice for synthesis of DNA in an amplification reaction.

Steps (ii) to (iv) will generally be repeated of the order twenty times or more as with conventional amplification methods.

The method according to the invention can be used for linear amplification of DNA or for the more usual exponential amplification. It will be appreciated, however, that for exponential amplification, a primer is required for each strand of the duplex DNA to be amplified.

While not essential, the method of the invention can be conveniently carried out using apparatus according to the second embodiment. With regard to that embodiment, the apparatus is like that described in the international application referred to above—PCT/AU98/00277—the entire content of which is incorporated herein by cross-reference. However, the PCT/Au98/00277 device is modified to include the infrared heater and optical detection systems.

In broad terms, the apparatus chamber can be any suitable, typically insulated, container for the internal device components and for association of ancillary components therewith. The chamber advantageously has a lid or sealable opening for loading the device rotor.

The temperature control of the apparatus chamber is effected by providing a heater linked to a temperature sensor so that a set temperature can be maintained. Typically, heating is by a heater located within the chamber with circulation of heated air within the chamber aided by a fan. Alternatively, heated air can be supplied to the chamber from a port or ports in a chamber wall.

Temperature control can also include a cooling system. For example, air supply to the chamber can be provided wherein the air is either at ambient temperature or less than ambient by passage through or over a cooling means. The temperature sensor referred to above is advantageously linked to the cooling system.

Rotors are typically a flat disc with an annular ring forming an outward portion thereof which is angled upwardly and has apertures therein for holding a plurality of reaction vessels which can be flat, vertical or angled in orientation. The rotor can be a disposable item which is used for a single set of amplifications.

The rotor drive means can be any drive means used for rotor devices in scientific equipment. For example, the drive means can be a direct-coupled AC motor, a DC motor, or an AC motor that drives the rotor via a gearbox or pulleys or the like. Preferably, the drive means is a direct-coupled AC motor, DC motor or stepper motor with the motor external to the chamber.

The infrared heater can be any suitable heater but is advantageously capable of delivering at least 100 watts. A preferred heater is a stainless steel tube with an outer diameter of approximately 2 mm and an internal diameter of 1.5 mm or a ni-chrome element wound in a spiral configuration. The heater is conveniently located at the bottom of the apparatus chamber in close proximity to the rotating reaction vessels. The stainless steel tube is advantageously mounted on ceramic insulators that are fixed to a metal reflector plate located at the bottom of the chamber. The reflector directs energy to the reaction vessels, has a large surface area, and has a low thermal mass. During infrared optical denaturation, the non-infrared heating system used for holding lower temperatures of 50 to 65° C. is deactivated. As a consequence of this, only the tips of reaction vessels are heated by the infrared energy. Once optical denaturation is complete, the non-infrared heating system is activated and the chamber cooled to the lower temperature of 50 to 65° C.

The optical system comprises a light source and detector. These components can be any of the light sources and detectors known to those of skill in the art. For example, the light source can be an LED, a laser light source or a halogen lamp, with an appropriate filter to provide light of an appropriate wavelength for excitation of the fluorophore in the reaction mixture. Emitted fluorescence is typically filtered and then measured by a photomultiplier tube, CCD array, photodiode or CCD camera.

The fluorescence detector of the optical system can also be used to monitor the progress of a reaction. For example, the level of fluorescence prior to denaturation can be used to assess the amount of DNA synthesised. Devices can furthermore include additional monitoring equipment such as a spectrophotometer or photometer. The additional monitoring equipment can be dedicated to assessing the progress of a reaction while the fluorescence detector of the optical system can be dedicated to its role in detection of denaturation. However, a photomultiplier used to detect reference sample optical denaturation can also be used to monitor sample fluorescence during the reaction.

Apparatus according to the invention can have associated herewith a computer for controlling such operations as:

rotor start up and speed (any speed greater than 10 rpm or even as low as 1 rpm is suitable but typically rotors are rotated at 500 rpm);

the annealing and polymerisation temperatures and the time for each of these steps;

operation of the infrared heater during denaturation of DNA;

processing of data generated by the optical system and any system used to measure the amount of DNA synthesised;

rotor braking; and cooling of the device chamber if necessary such as at the beginning and end of the amplification.

It will be appreciated that the computer can be used to control any other equipment or mechanisms associated with the device.

Because apparatus according to the invention has a dedicated (infrared) heater for denaturation of DNA, the chamber (convection) heater can be deactivated during the denaturation step along with the re-circulating blower (5). Typically, the chamber heater (5) is not activated until the denaturation step has been executed and any cooling of the chamber has been terminated.

Having broadly described the embodiments of the invention, an apparatus and use thereof will now be exemplified with reference to the accompanying drawings briefly described hereafter.

DETAILED DESCRIPTION OF PREFERRED EMBODIMENTS

Figure 1:
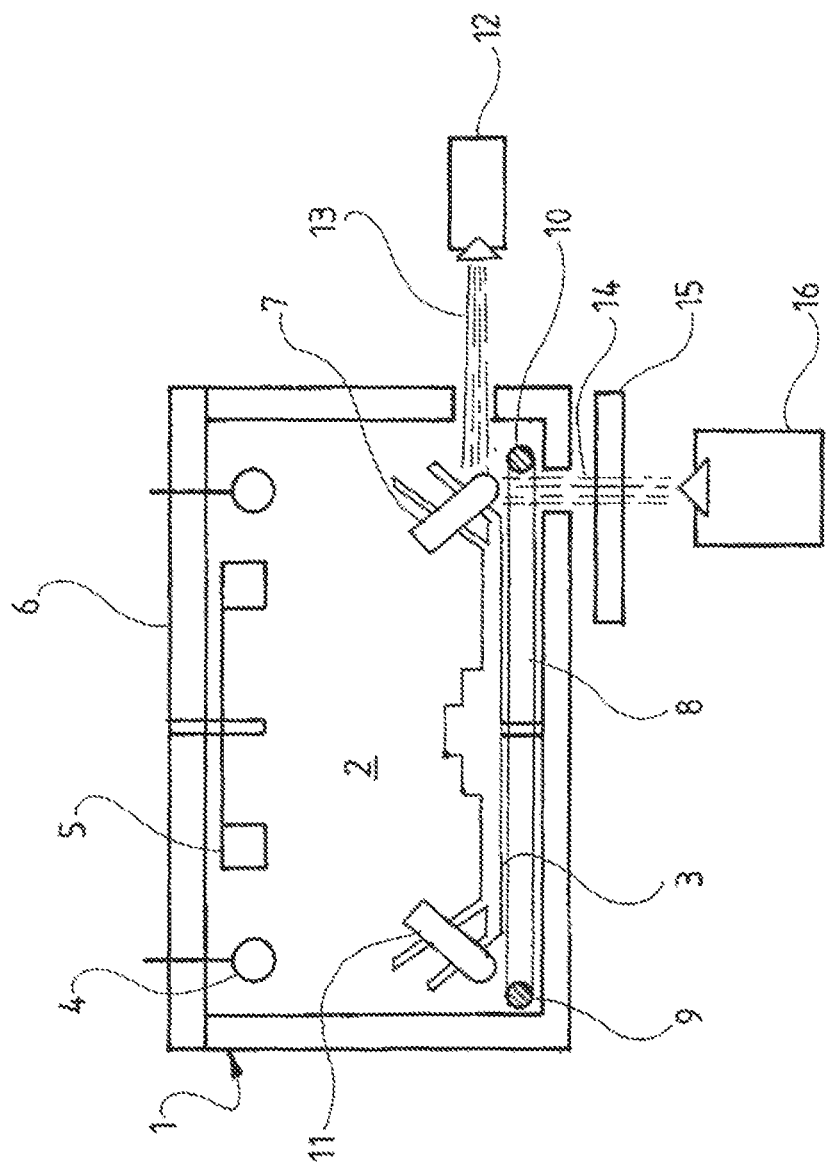
FIG. 1 is a schematic cross-sectional view of apparatus according to the invention.
Figure 2:
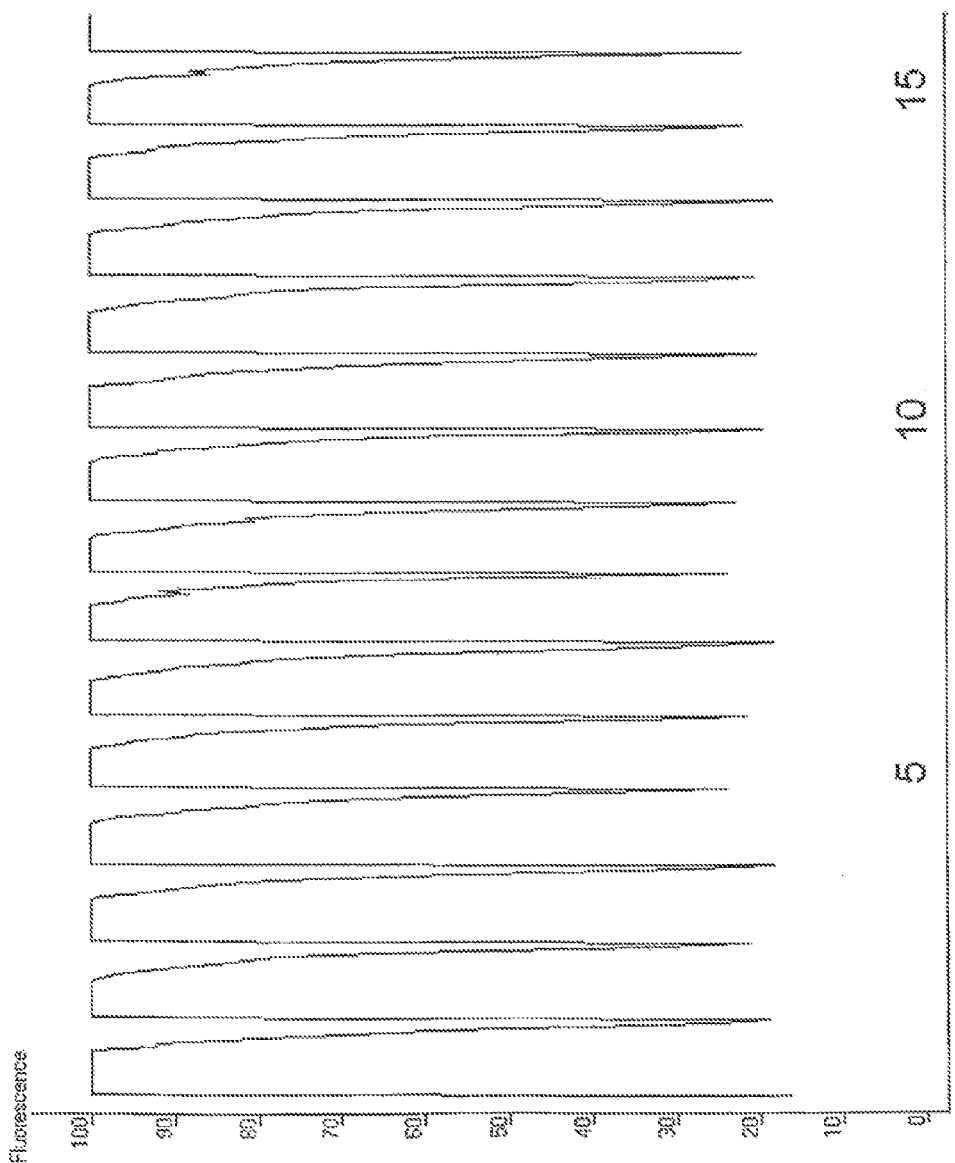
FIG. 2 is a graph of fluorescence emitted from a reference sample subjected to an amplification protocol.
Figure 3:
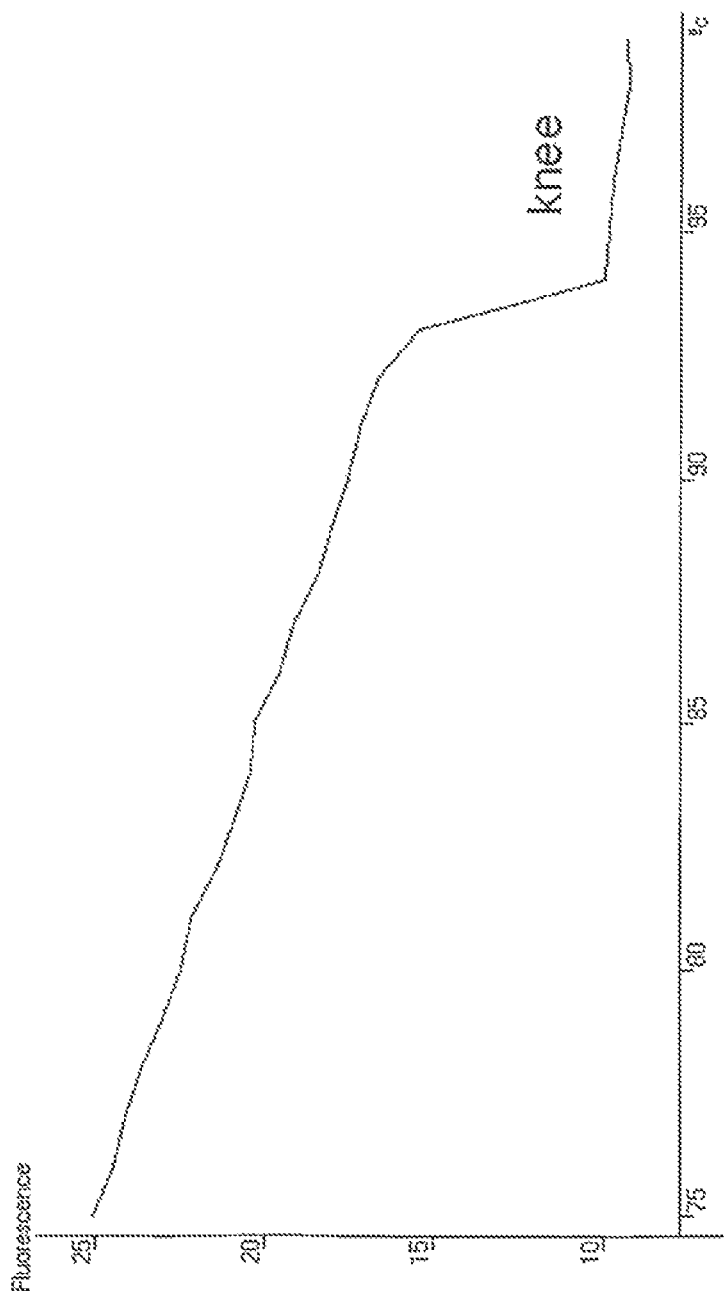
FIG. 3 is a graph of fluorescence emitted by a reference mixture during a denaturation step.
Figure 4:
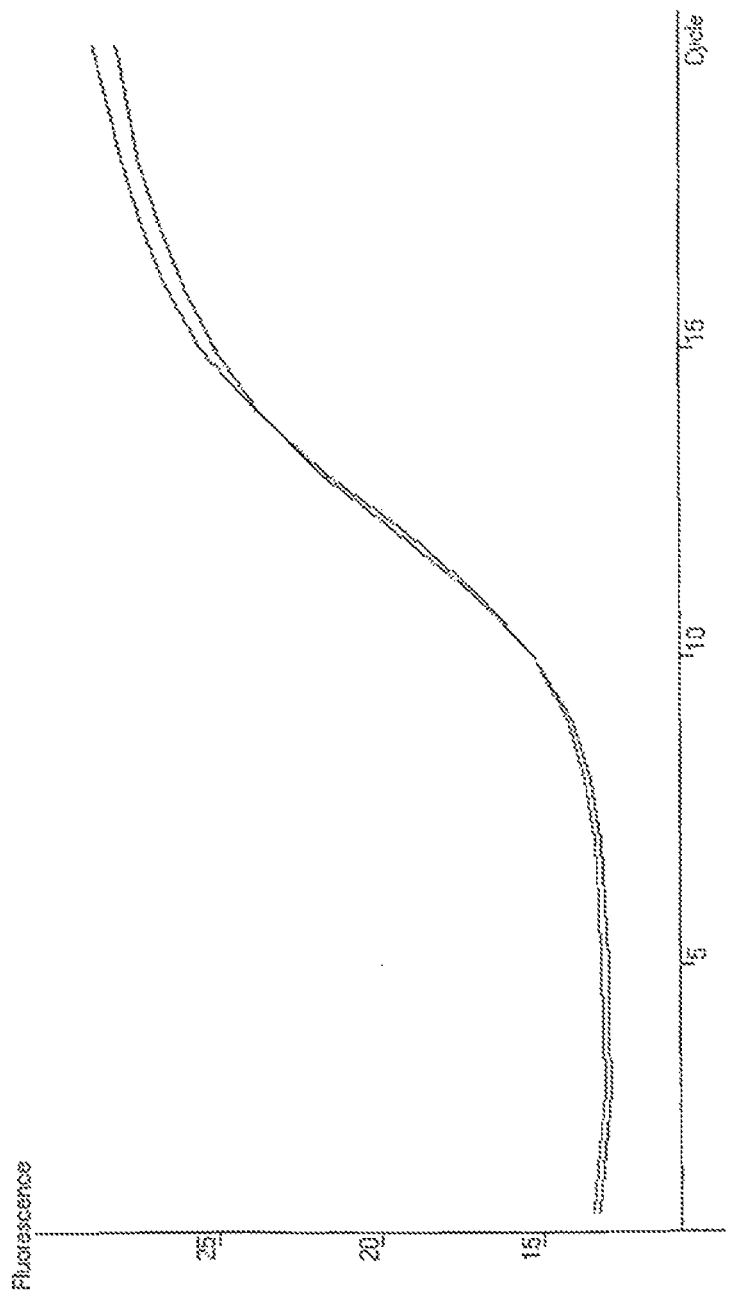
FIG. 4 is a graph of fluorescence emitted by an actual reaction mixture when measured at the end of each DNA synthesis step over the total number of cycles.

With reference to FIG. 1, apparatus 1 comprises a cylindrical chamber 2 having rotor 3 which is driven by a stepper motor not shown in the drawing. Chamber 2 also includes a radial heater 4 and a fan 5 for distributing heated air throughout the chamber. Heater 4 and fan 5 are mounted to hinged lid 6 of the device, which lid can be pivoted out of the way to gain access to rotor 3. Rotor 3 has a plurality of holes for holding reaction vessels, one of which vessels is item 7.

Device 1 also includes an infrared heater 8 at the bottom of chamber 2. Since chamber 2 is circular in cross section, heater 8 is also circular, items 9 and 10 being cross-sections of the heater. The position of heater 8 at the bottom of the chamber places it near reaction vessels in rotor 3, two such vessels being the previously-identified item 7, and item 11 of the drawing. A light source 12 is provided for illuminating a reaction vessel as it passes through beam 13. Light 14 emitted from reaction vessel 7 passes through filter 15 to be detected by photomultiplier tube 16.

Device components such as the rotor drive, heater 4, fan 5, infrared heater 8, and light source 12, are controlled by a computer not shown in the drawing.

Operation of the device is as follows. Reaction mixtures are dispensed into reaction vessels using manual pipettors or automated robotic pippetting means and heated to the denaturation temperature to activate the enzyme via heater 4 and fan 5 under the control of the associated computer. Rotor 3 is rotated at greater than 10 rpm under the control of the computer during this step and subsequent steps to average reaction vessel temperatures. The reaction tubes are then cooled to the annealing/extension temperature as usually both steps can be combined in the single temperature of approximately 60° C.

On command from the computer to denature double stranded DNA present in reaction mixtures, infrared heater 8 is activated. At that point, the chamber heater 4 and fan 5 are deactivated and are not reactivated until the denaturation step has ended. At least one reaction mixture or a reference mixture contains an intercalating dye such as ethidium bromide or SYBR™ Green. The dye is excited by light source 12 and fluorescence measured by photomultiplier tube 16 after selection of light of the appropriate wavelengths by filter 15. Fan 5 can be left on at a low speed during this step if desired. This has the effect of minimizing the surface temperature of each reaction vessel and prevents empty vessels from melting during optical denaturation. The time taken to perform an optical denaturation can be increased by this variation however.

With denaturation of the double stranded DNA, fluorescence emission diminishes and on reaching a preset level causes the computer to deactivate infrared heater 8.

On shut down of infrared heater 8, chamber 2 is cooled to the annealing temperature through the action of a cooling system not shown in the drawing. At the annealing temperature, the progress of the reaction can be monitored by way of a fluorescent probe present in reaction mixtures or by measuring the increased energy of the intercalating dye referred to above. This monitoring is by way of light source 12, filter 15 and photomultiplier tube 16. Results can be recorded by the computer.

Repetition of the above steps results in amplification of the DNA present in reaction mixtures. In the following example, greater detail of the role of the optical system is given.

A reaction mixture was prepared comprising the following:

| Reagent | Final Concentration (in 25 μl) | 1 × 25 Reaction (μl) | Master Mix (μl) |
|---|---|---|---|
| dH$_2$O | — | 10.95 | 219 |
| 10× buffer | 1× | 2.5 | 50 |
| MgCl$_2$ (50 mM) | 3 mM | 1.5 | 30 |
| dNTP (2.5 mM) | 0.2 mM | 2.0 | 40 |
| GAPDH-For (2.5 μM) | 0.3 μM | 3.0 | 60 |
| GAPDH-Rev (2.5 μM) | 0.3 μM | 3.0 | 60 |
| SG (1:1000) | 1:31250 | 0.8 | 16 |
| Taq Polymerase (5 U/μl) | 0.05 U/μl | 0.25 | 5 |
| DNA template | 3 × 10$^8$ to 3 × 10$^3$ copies | 1.0 | — |

The mixture contained in a 0.2 ml Eppendorf™ tube was loaded into the rotor of the apparatus exemplified above. After rotor activation, the following steps were carried out:

1) an optical denaturation command was issued by the computer;

2) the chamber was cooled to 60° C. and held at that temperature for 15-60 seconds for data acquisition;

3) an optical denaturation command was issued by the computer;

4) on denaturation of the DNA, the chamber was cooled to the hold temperature of (2) and held for the same time as in (2) for annealing of primer and DNA synthesis to occur; and 5) steps (3) and (4) were repeated for a further 14 cycles.

The following were effected by the optical denaturation command:

a) infrared heater 8 was turned on and heater 4 and fan 5 turned off;

b) a reference the containing DNA and an intercalating dye was monitored by the optical system at approximately 2 to 10 measurements per second;

c) on detection of DNA denaturation, heater 8 was turned off and the hold temperature re-established.

The invention claimed is:

1. A method for the amplification of DNA, the method comprising the steps of:
   i) forming a reaction mixture comprising said DNA, an oligonucleotide primer complementary to at least one strand of said DNA, nucleotides, and a thermostable DNA polymerase;
   ii) heating said mixture and a thermochromic liquid crystal simultaneously to a desired denaturation temperature;
   iii) optically detecting the clearing point of said thermochromic liquid crystal, and upon said optical detection allowing said mixture to cool to a temperature at which primer anneals to its complementary strand;
   iv) incubating said mixture at a temperature which allows synthesis of a DNA strand complementary to the strand to which said at least one primer anneals; and
   v) repeating steps (ii) to (iv) until the desired level of amplification is attained.

2. The method according to claim 1, wherein thermochromic liquid crystal has a clearing point or a color transition point within the range of 92-95° C.

3. The method according to claim 1, wherein in step (iii) cooling is aided by supplying a cooling agent to the environment of said reaction mixtures.

4. The method according to claim 1, wherein said annealing temperature is within the range of 50-65° C.

5. The method according to claim 1, wherein said steps (ii) to (iv) are repeated at least twenty times.

6. The method according to claim 1, wherein said amplification of DNA is linear or exponential.

\* \* \* \* \*